United States Patent
Zhang et al.

(10) Patent No.: US 11,379,609 B2
(45) Date of Patent: Jul. 5, 2022

(54) HEALTH FILE ACCESS CONTROL SYSTEM AND METHOD IN ELECTRONIC MEDICAL CLOUD

(71) Applicant: XI'AN UNIVERSITY OF POSTS AND TELECOMMUNICATIONS, Xi'an (CN)

(72) Inventors: Yinghui Zhang, Xi'an (CN); Dong Zheng, Xi'an (CN); Qinglan Zhao, Xi'an (CN); Chengzhe Lai, Xi'an (CN); Rui Guo, Xi'an (CN)

(73) Assignee: XI'AN UNIVERSITY OF POSTS AND TELECOMMUNICATIONS, Xi'an (CN)

( * ) Notice: Subject to any disclaimer, the term of this patent is extended or adjusted under 35 U.S.C. 154(b) by 852 days.

(21) Appl. No.: 16/315,648

(22) PCT Filed: Dec. 11, 2017

(86) PCT No.: PCT/CN2017/115412
§ 371 (c)(1),
(2) Date: Jan. 6, 2019

(87) PCT Pub. No.: WO2019/080281
PCT Pub. Date: May 2, 2019

(65) Prior Publication Data
US 2019/0354714 A1    Nov. 21, 2019

(30) Foreign Application Priority Data
Oct. 25, 2017  (CN) .......................... 201711006385.2

(51) Int. Cl.
*G06F 21/62* (2013.01)
*G16H 10/60* (2018.01)
(Continued)

(52) U.S. Cl.
CPC ........ *G06F 21/6245* (2013.01); *G06F 21/602* (2013.01); *G16H 10/60* (2018.01);
(Continued)

(58) Field of Classification Search
CPC .................................................. G06F 21/6245
See application file for complete search history.

(56) References Cited

U.S. PATENT DOCUMENTS 9,280,684 B1 * 3/2016 Kragh ................. G06F 21/6227
2012/0072723 A1 * 3/2012 Orsini ................. G06F 21/6218
713/165

(Continued)

OTHER PUBLICATIONS

Attribute-Based Data Sharing Scheme Revisited in Cloud Computing Shulan Wang, Kaitai Liang, Joseph K. Liu, Member, IEEE, Jianyong Chen, Jianping Yu, Weixin Xie 1556-6013 (c) 2015 IEEE. DOI 10.1109/TIFS.2016.2549004 (Year: 2015).*

(Continued)

*Primary Examiner* — Simon P Kanaan

(57) ABSTRACT

The present invention provides a health file access control system and method in an electronic medical cloud. The system comprises: a medical management center unit configured to generate a system public key and a system private key, and generate a private key for corresponding utilizer's attributes according to the system public key, the system private key, and a set of utilizer's attributes; an electronic medical cloud storage unit configured to receive and store a privacy-protected health file ciphertext; and at least one health file user access unit configured to encrypt the health file according to the system public key to obtain the privacy-protected health file ciphertext, and/or generate the set of utilizer's attribute, and decrypt the privacy-protected health file ciphertext according to the system public key and the private key for utilizer's attributes. The health file access control system and method in the electronic medical cloud (Continued)

provided by the present invention not only ensure the confidentiality of the health file, but also improve the security and calculation efficiency of the health file access.

19 Claims, 6 Drawing Sheets

(51) Int. Cl.
    *G06F 21/60*     (2013.01)
    *H04L 9/08*     (2006.01)
    *H04L 9/30*     (2006.01)
    *H04L 9/40*     (2022.01)

(52) U.S. Cl.
    CPC .............. *H04L 9/0869* (2013.01); *H04L 9/30* (2013.01); *H04L 63/0435* (2013.01); *G06F 2221/2107* (2013.01)

(56) References Cited

U.S. PATENT DOCUMENTS

2016/0366233 A1* 12/2016 Le .............................. G06F 8/65
2018/0020001 A1* 1/2018 White ................. H04L 63/0428
2019/0354714 A1* 11/2019 Zhang ................... H04L 9/0825

OTHER PUBLICATIONS

Yinghui Zhang, "Cloud-based data sharing scheme with preserved privacy and supported attribute extension", Journal of Xi'An University of Posts and Telecommunications vol. 20, No. 5, Sep. 2015, 5 pages, Xi'An, China.

* cited by examiner

HEALTH FILE ACCESS CONTROL SYSTEM AND METHOD IN ELECTRONIC MEDICAL CLOUD

RELATED APPLICATIONS

This application is a United States National Stage Application filed under 35 U.S.C 371 of PCT Patent Application Serial No. PCT/CN2017/115412, filed Dec. 11, 2017, which claims Chinese Patent Application Serial No. 201711006385.2, filed Oct. 25, 2017, the disclosure of all of which are hereby incorporated by reference in their entirety.

TECHNICAL FIELD

The present invention relates to the field of information security technologies, and in particular, to a health file access control system and method in an electronic medical cloud.

BACKGROUND

With the rapid development of technologies such as wireless communication and cloud computing, the application prospects of electronic medical cloud in the medical industry become more promising. Currently, however, most medical information systems still have serious "island" and "chimney" phenomena at multiple levels. The main reasons for such phenomena are as follows. First, little information is communicated between medical fields and public health, hospitals and communities. Second, little information is exchanged between different institutions of the same field, or between different departments within the same institution. In some institutions, several different systems may be used by the same department, the same position or even the same person, as a result, information cannot be shared. In addition, medical information and cloud platforms face many security threats. In 2017, WannaCry ransomware attacked the medical institutions, large enterprise intranets and government agencies across the world, resulting in a paralysis of medical information systems in multiple regions, affecting more than 100 countries around the world, causing serious threats for important data and user privacy. According to the 360 China Security Website's 2015 China Website Security Report, a total of 1410 vulnerabilities in 2015 may result in the disclosure of personal information on the website. The amount of personal information that may or may have been leaked is as high as 5.53 billion pieces. From the average amount of information leaked by each vulnerability, the medical and health industry ranks first.

At present, most studies consider the use of cryptography to protect the privacy of medical data, that is, to encrypt the data such as health files by, for example, identity-based encryption, predicate encryption, and attribute-based encryption before uploading the data to the cloud server. Compared with other encryption schemes, attribute-based encryption can achieve fine-grained access control while protecting data confidentiality without predicting the identity information of data users. As a new "one-to-many" encryption mode, attribute-based encryption is widely used for fine-grained data sharing in cloud environments. According to the access strategy, attribute-based encryption can be classified into two types: key-policy attribute-based encryption and ciphertext-policy attribute-based encryption. However, most ciphertext-policy attribute-based encryption schemes cannot protect user's attribute privacy since the user's attribute value is directly exposed in the cipher text. As a result, they cannot be used for access control of sensitive data such as personal health files. In medical data access control, attribute privacy protection is very important. For example, the access policy corresponding to a personal health file ciphertext may contain the attribute of the diagnosis and treatment department and the value of the attribute is directed to the heart disease department. If the ciphertext can be accessed and the access policy is directly exposed in the ciphertext, then anyone knows that this user has a heart disease, resulting in serious violation of personal privacy. In addition, the existing attribute-hiding attribute-based encryption schemes have drawbacks such as high decryption computation complexity, inability to support large attribute domains, and inflexible access policies.

SUMMARY

In view of the problems existing in the prior art, the present invention provides a health file access control system and method in an electronic medical cloud.

According to an aspect of the present invention, a health file access control system in an electronic medical cloud is provided, the system comprising: a medical management center unit, an electronic medical cloud storage unit, and at least one health file user access unit; wherein the medical management center unit is configured to generate a system public key and a system private key, and generate a private key for corresponding utilizer's attributes according to the system public key, the system private key, and a set of utilizer's attributes sent by the at least one health file user access unit; the electronic medical cloud storage unit is configured to receive and store a privacy-protected health file ciphertext sent by the at least one health file user access unit; and the at least one health file user access unit is configured to encrypt the health file according to the system public key sent by the medical management center unit to obtain the privacy-protected health file ciphertext, and/or generate the set of utilizer's attributes, and decrypt the privacy-protected health file ciphertext sent by the electronic medical cloud storage unit according to the system public key and the private key for utilizer's attributes sent by the medical management center unit.

According to another aspect of the present invention, a health file access control method in an electronic medical cloud is provided, the method comprising:

performing, by a medical management center unit, system initialization to generate a system public key PK and a system private key MK (S101);

inputting, by at least one health file user access unit, basic information and/or health care information of a health file owner to generate a health file M (S102);

encrypting, by the at least one health file user access unit, the health file M according to the system public key PK to obtain a privacy-protected health file ciphertext CT (S103); and storing the privacy-protected health file ciphertext CT into an electronic medical cloud storage unit (S104).

According to still another aspect of the present invention, a health file access control method in an electronic medical cloud is provided, the method comprising:

performing, by a medical management center unit, system initialization to generate a system public key PK and a system private key MK (S101');

inputting, by at least one health file user access unit, basic information of a health file utilizer to generate a set of utilizer's attributes S (S102');

performing, by the medical management center unit, registration for a new user and generating a private key for utilizer's attributes $SK_S$ according to the system public key PK, the system private key MK, and the set of utilizer's attributes S (S103');

downloading, by the at least one health file user access unit, a privacy-protected health file ciphertext CT from an electronic medical cloud storage unit (S104'); and decrypting, by the at least one health file user access unit, the privacy-protected health file ciphertext CT sent by the electronic medical cloud storage unit according to the system public key PK and the private key for utilizer's attributes $SK_S$ to obtain a health file M (S105').

The health file access control system and method in the electronic medical cloud provided by the present invention have the following beneficial effects:

1. A secure electronic medical cloud information storage system and method is established to achieve fine-grained access control of health files while keeping data confidential.

2. The attribute privacy protection is achieved under the premise of ensuring the confidentiality of health files. That is, the health file owner is able to hide the attribute value corresponding to the access policy in the privacy-protected health file ciphertext, while the health file utilizer is able to perform an efficient decryption test without the access policy attribute value, and determine whether the private key for utilizer's attributes can decrypt the health file ciphertext including the basic information and/or health care information of the health file owner.

3. The size of the system public key is constant, computational complexity of the decryption test is low, only a constant bilinear pair is needed, and the decryption does not require attribute value information, thereby simplifying the system and method, and improving computational efficiency and protecting attribute privacy while keeping the system and method secure.

BRIEF DESCRIPTION OF THE DRAWINGS

To make the technical solution of the embodiments of the present invention or the prior art clearer, the accompanying drawings for illustrating the embodiments of the present invention or the prior art are outlined below. Apparently, the accompanying drawings are used for illustration only, and those skilled in the art can derive other drawings from such accompanying drawings without creative efforts.

DETAILED EMBODIMENTS

With reference to the accompanying drawings, the technical solution of the embodiments of the present invention is described clearly and completely as following. It should be understood that, the given embodiments are only parts of the embodiments of the present invention, but not all embodiments of the present invention. All other embodiments obtained by a person of ordinary skill in the art based on the embodiments of the present invention without creative efforts shall fall within the protection scope of the present invention.

Figure 1:
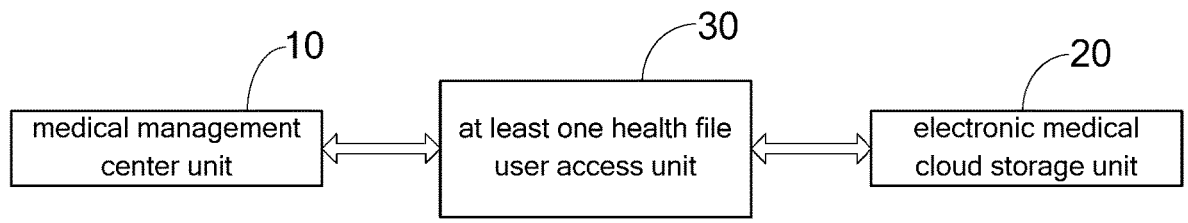
FIG. 1 depicts a block diagram showing a module structure of a health file access control system in an electronic medical cloud according to the present invention.

FIG. 1 depicts a block diagram showing a module structure of a health file access control system in an electronic medical cloud according to the present invention. As shown in FIG. 1, the health file access control system in an electronic medical cloud provided according to the present invention comprises: a medical management center unit 10, an electronic medical cloud storage unit 20, and at least one health file user access unit 30; wherein the medical management center unit 10 is configured to generate a system public key and a system private key, and generate a corresponding utilizer attribute private key according to the system public key, the system private key, and a set of utilizer's attributes sent by the at least one health file user access unit 30; the electronic medical cloud storage unit 20 is configured to receive and store a privacy-protected health file ciphertext sent by the at least one health file user access unit 30; and the at least one health file user access unit 30 is connected to the medical management center unit 10 and the electronic medical cloud storage unit 20, and configured to encrypt the health file according to the system public key sent by the medical management center unit 10 to obtain the privacy-protected health file ciphertext, and/or generate the set of utilizer's attributes, and decrypt the privacy-protected health file ciphertext sent by the electronic medical cloud storage unit 20 according to the system public key and the private key for utilizer's attributes sent by the medical management center unit 10.

Figure 2:
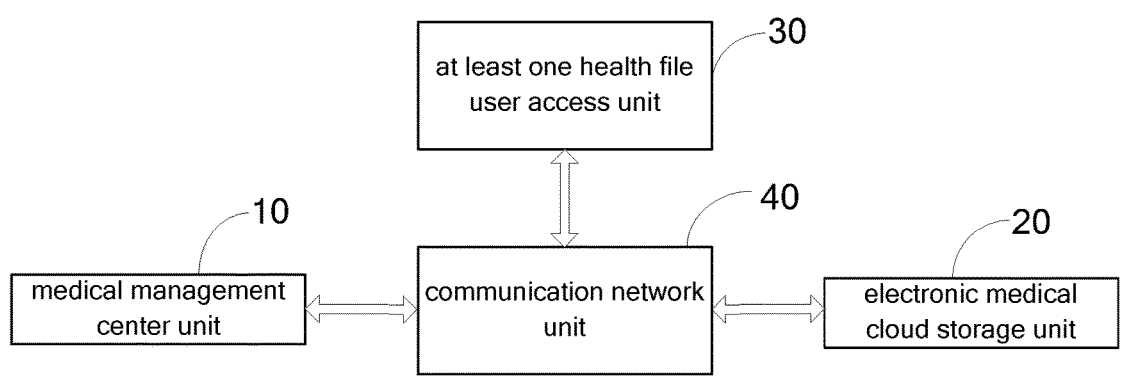
FIG. 2 depicts a block diagram showing another module structure of a health file access control system in an electronic medical cloud according to the present invention.

In an optional embodiment as shown in FIG. 2, the health file access control system in the electronic medical cloud provided by the present invention further comprises a communication network unit 40 connected to the medical management center unit 10, the electronic medical cloud storage unit 20, and the at least one health file user access unit 30, respectively in a wireless or wired manner for communication between the medical management center unit 10 and the at least one health file user access unit 30, and/or between the electronic medical cloud storage unit 20 and the at least one health file user access unit 30.

In the health file access control system in the electronic medical cloud shown in FIG. 1 and FIG. 2, the number of the health file user access units 30 may be one or more, which is not limited herein.

For the purpose of description, and in order to enable those skilled in the art to better understand the health file access control system in the electronic medical cloud provided by the present invention, in the first to third examples the health file access control system is described in detail with the system comprising one health file user access unit as an example.

Figure 3:
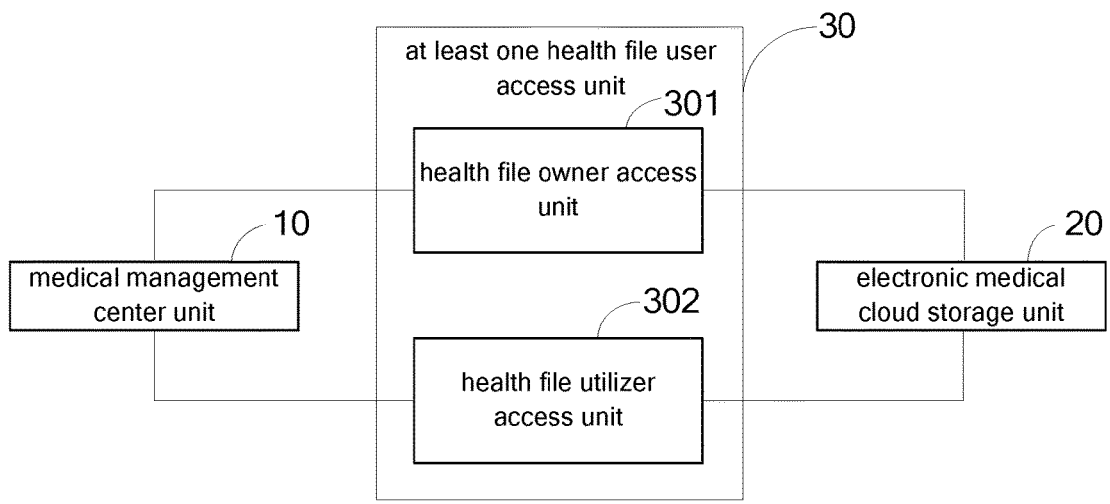
FIG. 3 depicts a block diagram showing a module structure of a first example of a health file access control system in an electronic medical cloud according to the present invention.

FIG. 3 depicts a block diagram showing a module structure of a first example of a health file access control system in an electronic medical cloud according to the present invention. As shown in FIG. 3, the health file access control system in the electronic medical cloud comprises: a medical management center unit 10, an electronic medical cloud storage unit 20, and a health file user access unit 30; wherein the medical management center unit 10 is configured to generate a system public key and a system private key, and generate a private key corresponding to utilizer's attributes according to the system public key, the system private key, and a set of utilizer's attributes sent by the health file user access unit 30; the electronic medical cloud storage unit 20 is configured to receive and store a privacy-protected health file ciphertext sent by the health file user access unit 30; and the health file user access unit 30 is connected to the medical management center unit 10 and the electronic medical cloud storage unit 20, and configured to encrypt the health file according to the system public key sent by the medical management center unit 10 to obtain the privacy-protected health file ciphertext, and/or generate the set of utilizer's attributes, and decrypt the privacy-protected health file ciphertext sent by the electronic medical cloud storage unit 20 according to the system public key and the private key for utilizer's attributes sent by the medical management center unit 10.

Further, as shown in FIG. 3, the health file user access unit 30 comprises a health file owner access unit 301 and a health file utilizer access unit 302. The health file owner access unit 301 is connected to the medical management center unit 10 and the electronic medical cloud storage unit 20, respectively and configured to encrypt the health file according to the system public key sent by the medical management center unit 10 to obtain a privacy-protected health file ciphertext and send the privacy-protected health file ciphertext to the electronic medical cloud storage unit 20. The health file utilizer access unit 302 is connected to the medical management center unit 10 and the electronic medical cloud storage unit 20, respectively and configured to generate a set of utilizer's attributes, and decrypt the privacy-protected health file ciphertext sent by the electronic medical cloud storage unit 20 according to the system public key and the private key for utilizer's attributes sent by the medical management center unit 10.

The medical management center unit 10 is specifically configured to: (1) perform system initialization, generate a system public key and a system private key, and disclose the system public key and keep the system private key confidential; and (2) execute health file user registration and generate a private key which corresponds to utilizer's attributes according to the system public key, the system private key, and a set of utilizer's attributes sent by the health file utilizer access unit 302.

The electronic medical cloud storage unit 20 is specifically configured to: (1) receive and store a privacy-protected health file ciphertext sent by the health file owner access unit 301; and (2) send the stored privacy-protected health file ciphertext to the health file utilizer access unit 302.

The health file owner access unit 301 is specifically configured to: (1) input basic information and/or health care information of the health file owner to generate a health file; (2) select a symmetric key from the key space of the advanced encryption standard according to the system public key sent by the medical management center unit 10, and perform a symmetric encryption algorithm of the advanced encryption standard for the health file according to the system public key sent by the medical management center unit 10 and the selected symmetric key to obtain a file symmetric ciphertext; (3) select an access policy according to the system public key sent by the medical management center unit 10; (4) perform attribute-hiding attribute-based encryption on the symmetric key according to the selected access policy to generate a symmetric key ciphertext; and (5) generate a privacy-protected health file ciphertext according to the file symmetric ciphertext and the symmetric key ciphertext, and send the privacy-protected health file ciphertext to the electronic medical cloud storage unit 20.

The health file utilizer access unit 302 is specifically configured to: (1) download the privacy-protected health file ciphertext from the electronic medical cloud storage unit 20; (2) input basic information of the health file utilizer; (3) generate a set of utilizer's attributes according to the basic information of the health file utilizer; (4) parse the privacy-protected health file ciphertext sent by the electronic medical cloud storage unit 20 into a file symmetric ciphertext and a symmetric key ciphertext; (5) perform attribute-hiding attribute-based decryption on the symmetric key ciphertext according to the private key for utilizer's attribute sent by the medical management center unit 10 to obtain a symmetric key; and (6) perform a decryption algorithm of the advanced encryption standard for the file symmetric ciphertext according to the system public key sent by the medical management center unit 10 and the symmetric key obtained by performing attribute-hiding attribute-based decryption on the symmetric key ciphertext, to obtain a health file.

Specifically, there are several ways for the health file utilizer access unit 302 to download the privacy-protected health file from the electronic medical cloud storage unit 20. For example, the health file utilizer access unit 302 may generate target information comprising pre-downloaded privacy-protected health file ciphertext and send the target information to the electronic medical cloud storage unit 20. The electronic medical cloud storage unit 20 sends the corresponding privacy-protected health file ciphertext to the health file utilizer access unit 302 according to the target information. Of course, those skilled in the art can also select other methods as needed, which are not limited herein.

The health file access control system in the electronic medical cloud of the first example further comprises a communication network unit (not shown) connected to the medical management center unit 10, the electronic medical cloud storage unit 20, the health file owner access unit 301, and the health file utilizer access unit 302, respectively in a wireless or wired manner for communication between the medical management center unit 10 and the health file owner access unit 301, and/or between the medical management center unit 10 and the health file utilizer access unit 302, and/or between the electronic medical cloud storage unit 20 and the health file owner access unit 301, and/or between the electronic medical cloud storage unit 20 and the health file utilizer access unit 302.

Figure 4:
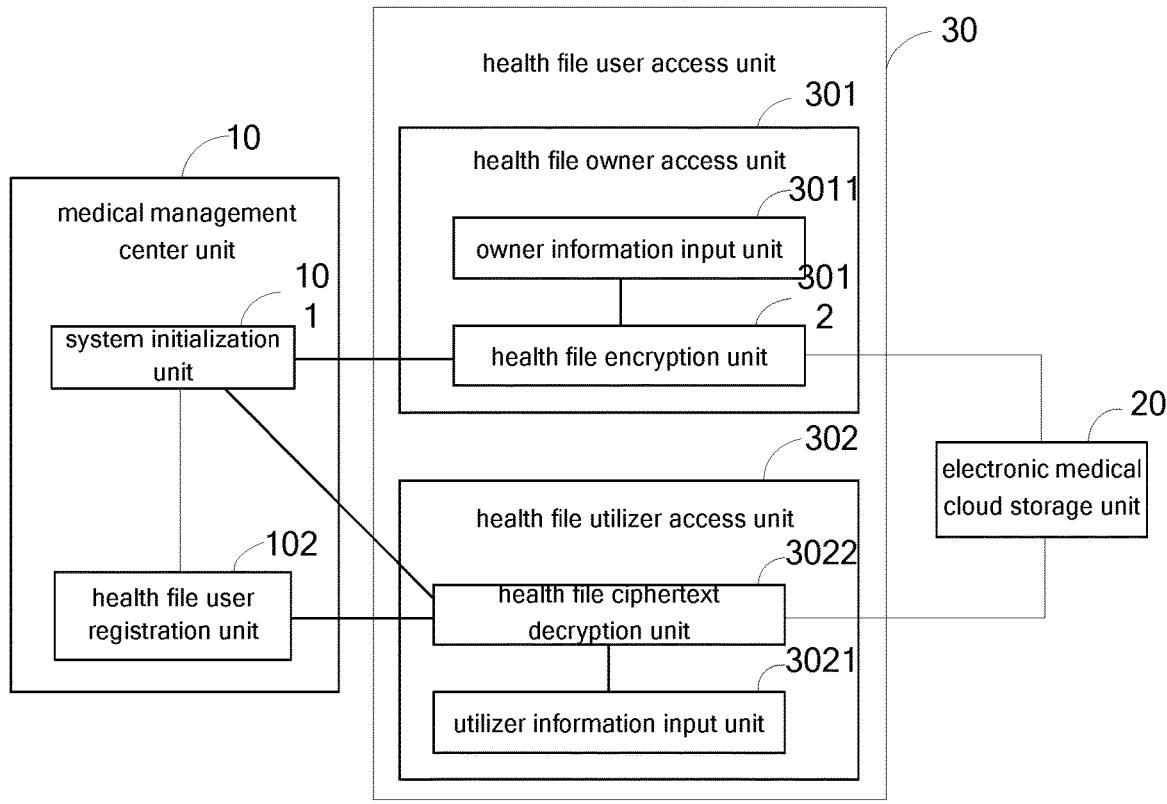
FIG. 4 depicts a block diagram showing another module structure of a first example of a health file access control system in an electronic medical cloud according to the present invention.

In an alternative embodiments of the first example, as shown in FIG. 4, the medical management center unit 10 comprises a system initialization unit 101 and a health file user registration unit 102; the health file owner access unit 301 in the health file user access unit 30 comprises an owner information input unit 3011 and a health file encryption unit 3012; the health file utilizer access unit 302 in the health file user access unit 30 comprises a utilizer information input unit 3021 and a health file ciphertext decryption unit 3022.

The system initialization unit 101 is configured to perform system initialization to generate a system public key and a system private key, and disclose the system public key and keep the system private key confidential; the health file user registration unit 102 is connected to the system initialization unit 101 and the health file ciphertext decryption unit 3022, respectively and configured to perform health file user registration and generate a private key corresponding to utilizer's attributes according to the system public key sent by the system initialization unit 101 and the set of utilizer's attributes sent by the health file ciphertext decryption unit 3022.

The owner information input unit 3011 is configured to input basic information and/or health care information of the health file owner to generate a health file; the health file encryption unit 3012 is connected to the system initialization unit 101, the electronic medical cloud storage unit 20, and the owner information input unit 3011, respectively and configured to encrypt the health file sent by the owner information input unit 3011 according to the system public key sent by the system initialization unit 101 to obtain a privacy-protected health file ciphertext, and send the privacy-protected health file ciphertext to the electronic medical cloud storage unit 20.

Further, the health file encryption unit 3012 is specifically configured to: (1) select a symmetric key from the key space of the advanced encryption standard according to the system public key sent by the system initialization unit 101, and perform a symmetric encryption algorithm of the advanced encryption standard for the health file sent by the owner information input unit 3011 according to the system public key sent by the medical management center unit 10 and the selected symmetric key to obtain a file symmetric ciphertext; (2) select an access policy according to the system public key sent by the system initialization unit 101; (3) perform attribute-hiding attribute-based encryption on the symmetric key according to the selected access policy to generate a symmetric key ciphertext; and (4) generate a privacy-protected health file ciphertext according to the file symmetric ciphertext and the symmetric key ciphertext, and send the privacy-protected health file ciphertext to the electronic medical cloud storage unit 20.

The utilizer information input unit 3021 is configured to input basic information of the health file utilizer; the health file ciphertext decryption unit 3022 is connected to the system initialization unit 101, the electronic medical cloud storage unit 20, and the utilizer information input unit 3021, respectively and configured to generate a set of utilizer's attribute according to the basic information of the health file utilizer sent by the utilizer information input unit 3021, and decrypt the privacy-protected health file ciphertext sent by the electronic medical cloud storage unit 20 according to the system public key sent by the system initialization unit 101 and the private key for utilizer's attribute sent by the health file user registration unit 102 to obtain a health file.

Further, the health file ciphertext decryption unit 3022 is specifically configured to: (1) download the privacy-protected health file ciphertext from the electronic medical cloud storage unit 20; (2) generate a set of utilizer's attribute according to basic information of the health file utilizer sent by the utilizer information input unit 3021; (3) parse the privacy-protected health file ciphertext sent by the electronic medical cloud storage unit 20 into a file symmetric ciphertext and a symmetric key ciphertext; (4) perform attribute-hiding attribute-based decryption on the symmetric key ciphertext according to the private key for utilizer's attribute sent by the health file user registration unit 102 to obtain a symmetric key; and (5) perform a decryption algorithm of the advanced encryption standard for the file symmetric ciphertext according to the system public key sent by the system initialization unit 10 and the symmetric key obtained by performing attribute-hiding attribute-based decryption on the symmetric key ciphertext to obtain a health file.

Specifically, the health file ciphertext decryption unit 3022 may download the privacy-protected health file from the electronic medical cloud storage unit 20 in various ways. For example, the health file ciphertext decryption unit 3022 may generate target information comprising pre-downloaded privacy-protected health file ciphertext and send the target information to the electronic medical cloud storage unit 20. The electronic medical cloud storage unit 20 sends the corresponding privacy-protected health file ciphertext to the health file utilizer access unit 302 according to the target information. Of course, those skilled in the art can also select other methods as needed, which are not limited herein.

In some alternative embodiments, the system may further comprise a communication network unit (not shown) connected to the system initialization unit 101, the health file user registration unit 102, the electronic medical cloud storage unit 20, the health file encryption unit 3012, and the health file ciphertext decryption unit 3022, respectively in a wireless or wired manner for communication between the system initialization unit 101 and the health file encryption unit 3012, and/or between the system initialization unit 101 and the health file ciphertext decryption unit 3022, and/or between the health file user registration unit 102 and the health file ciphertext decryption unit 3022, and/or between the electronic medical cloud storage unit 20 and the health file encryption unit 3012, and/or between the electronic medical cloud storage unit 20 and the health file ciphertext decryption unit 3022.

The health file user access unit in the health file access control system in the electronic medical cloud according to the first example is referred to here as user A access unit, its working principle is outlined as follows: user A access unit includes a health file owner access unit and a health file utilizer access unit, therefore, user A can not only input the basic information and/or health care information of the user A through the health file owner access unit to generate a health file, but also encrypt the generated health file through the health file utilizer access unit to generate a privacy-protected health file ciphertext, and send the privacy-protected health file ciphertext to the electronic medical cloud storage unit for storage. Also, the user A can download the privacy-protected health file ciphertext of user A or another user (for example, user B and/or user C) from the electronic medical cloud storage unit, input basic information of the health file utilizer through the health file utilizer access unit, and decrypt the privacy-protected health file ciphertext through the health file utilizer access unit to obtain the health file corresponding to the user A or another user (such as user B and/or user C) for review. In this system, the user A can not only encrypt the user A's own health file to generate a privacy-protected health file, but also decrypt the privacy-protected health file of user A or other users, thereby obtaining the corresponding health files for review.

Figure 5:
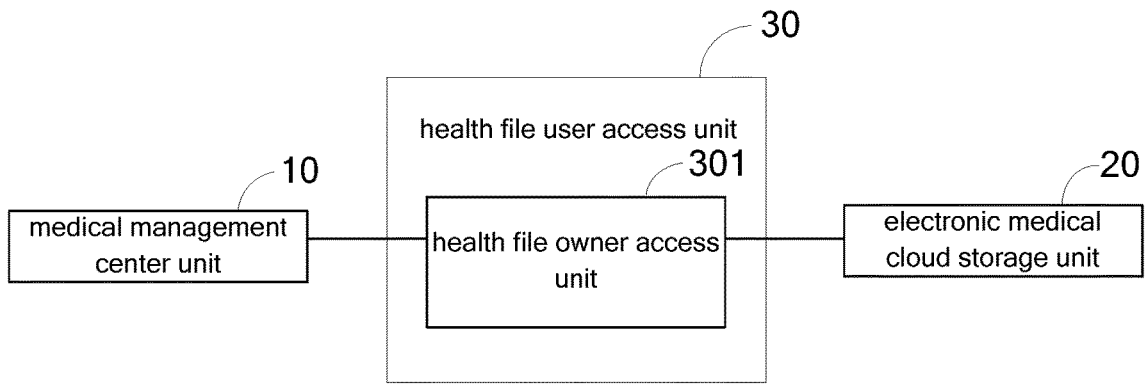
FIG. 5 depicts a block diagram showing a module structure of a second example of a health file access control system in an electronic medical cloud according to the present invention.

FIG. 5 is a block diagram showing a module structure of a second example of a health file access control system in an electronic medical cloud according to the present invention. As shown in FIG. 5, the health file access control system in the electronic medical cloud comprises: a medical management center unit 10, an electronic medical cloud storage unit 20, and a health file user access unit 30; wherein the medical management center unit 10 is configured to generate a system public key and a system private key, and generate a private key corresponding utilizer's attributes according to the system public key, the system private key, and a set of utilizer's attributes sent by the health file user access unit comprising a health file utilizer access unit (not shown); the electronic medical cloud storage unit 20 is configured to receive and store a privacy-protected health file ciphertext sent by the health file user access unit 30; and the health file user access unit 30 is connected to the medical management center unit 10 and the electronic medical cloud storage unit 20, respectively and configured to encrypt the health file according to the system public key sent by the medical management center unit 10 to obtain the privacy-protected health file ciphertext.

Further, as shown in FIG. 5, the health file user access unit 30 includes a health file owner access unit 301 connected to the medical management center unit 10 and the electronic medical cloud storage unit 20, respectively and configured to encrypt the health file according to the system public key sent by the medical management center unit 10 to obtain a privacy-protected health file ciphertext, and send the privacy-protected health file ciphertext to the electronic medical cloud storage unit 20.

The medical management center unit 10 is specifically configured to: (1) perform system initialization to generate a system public key and a system private key, and disclose the system public key and keep the system private key confidential; and (2) execute health file user registration and generate a private key for utilizer's attribute according to the system public key, the system private key, and a set of utilizer's attributes sent by the health file user access unit comprising a health file utilizer access unit (not shown).

The electronic medical cloud storage unit 20 is specifically configured to: (1) receive and store a privacy-protected health file ciphertext sent by the health file owner access unit 301; and (2) send the stored privacy-protected health file ciphertext to the health file user access unit comprising a health file utilizer access unit (not shown).

The health file owner access unit 301 is specifically configured to: (1) input basic information and/or health care information of the health file owner to generate a health file; (2) select a symmetric key from the key space of the advanced encryption standard according to the system public key sent by the medical management center unit 10, and perform a symmetric encryption algorithm of the advanced encryption standard for the health file according to the system public key sent by the medical management center unit 10 and the selected symmetric key to obtain a file symmetric ciphertext; (3) select an access policy according to the system public key sent by the medical management center unit 10; (4) perform attribute-hiding attribute-based encryption on the symmetric key according to the selected access policy to generate a symmetric key ciphertext; and (5) generate a privacy-protected health file ciphertext according to the file symmetric ciphertext and the symmetric key ciphertext, and send the privacy-protected health file ciphertext to the electronic medical cloud storage unit 20.

The health file access control system in the electronic medical cloud of the second example further comprises a communication network unit (not shown) connected to the medical management center unit 10, the electronic medical cloud storage unit 20, and the health file owner access unit 301, respectively in a wireless or wired manner for communication between the medical management center unit 10 and the health file owner access unit 301, and/or between the electronic medical cloud storage unit 20 and the health file owner access unit 301.

Figure 6:
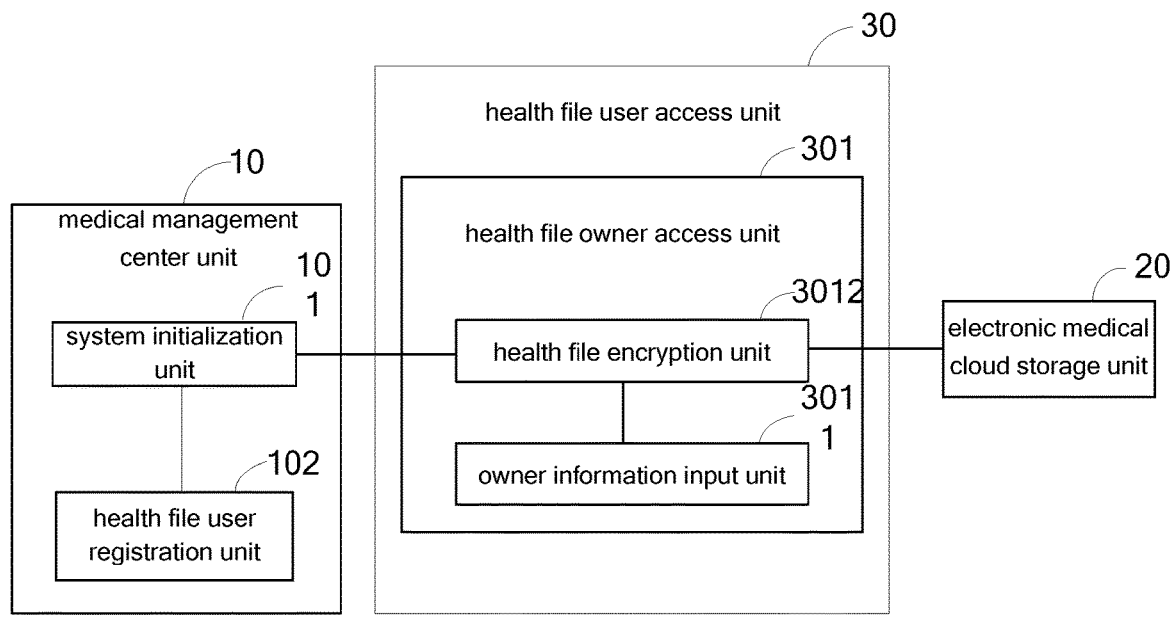
FIG. 6 depicts a block diagram showing another module structure of a second example of a health file access control system in an electronic medical cloud according to the present invention.

In some alternative embodiments of the second example, as shown in FIG. 6, the medical management center unit 10 comprises a system initialization unit 101 and a health file user registration unit 102; the health file owner access unit 301 in the health file user access unit 30 comprises an owner information input unit 3011 and a health file encryption unit 3012; wherein the system initialization unit 101 is configured to perform system initialization to generate a system public key and a system private key, and disclose the system public key and keep the system private key confidential; the health file user registration unit 102 is connected to the system initialization unit 101 and the health file user access unit comprising a health file utilizer access unit (not shown), respectively and configured to perform health file user registration and generate a private key for utilizer's attributes according to the system public key sent by the system initialization unit 101 and the set of utilizer's attribute sent by the health file user access unit comprising a health file utilizer access unit (not shown); the owner information input unit 3011 is configured to input basic information and/or health care information of the health file owner to generate a health file; and the health file encryption unit 3012 is connected to the system initialization unit 101, the electronic medical cloud storage unit 20, and the owner information input unit 3011, respectively and configured to encrypt the health file sent by the owner information input unit 3011 according to the system public key sent by the system initialization unit 101 to obtain a privacy-protected health file ciphertext, and send the privacy-protected health file ciphertext to the electronic medical cloud storage unit 20.

Further, the health file encryption unit 3012 is specifically configured to: (1) select a symmetric key from the key space of the advanced encryption standard according to the system public key sent by the system initialization unit 101, and perform a symmetric encryption algorithm of the advanced encryption standard for the health file sent by the owner information input unit 3011 according to the system public key sent by the medical management center unit 10 and the selected symmetric key to obtain a file symmetric ciphertext; (2) select an access policy according to the system public key sent by the system initialization unit 101; (3) perform attribute-hiding attribute-based encryption on the symmetric key according to the selected access policy to generate a symmetric key ciphertext; and (4) generate a privacy-protected health file ciphertext according to the file symmetric ciphertext and the symmetric key ciphertext, and send the privacy-protected health file ciphertext to the electronic medical cloud storage unit 20.

In some alternative embodiments, the system may further comprise a communication network unit (not shown) connected to the system initialization unit 101, the health file user registration unit 102, the electronic medical cloud storage unit 20, and the health file encryption unit 3012, respectively in a wireless or wired manner for communication between the system initialization unit 101 and the health file encryption unit 3012, and/or between the electronic medical cloud storage unit 20 and the health file encryption unit 3012.

It should be noted that, in the second example, if the health file user access unit comprising a health file utilizer access unit (not shown) does not send the set of utilizer's attribute, the medical management center unit 10 will not perform the operation of executing health file user registration and generating a private key for the utilizer's attribute according to the system public key, the system private key, and a set of utilizer's attribute sent by the health file user access unit comprising a health file utilizer access unit (not shown). Specifically, if the health file user access unit comprising a health file utilizer access unit (not shown) does not send the set of utilizer's attributes, the health file user registration unit 102 in the medical management center unit 10 will not perform the operation of executing health file user registration and generating a private key for corresponding utilizer's attributes according to the system public key, the system private key, and a set of utilizer's attributes sent by the health file user access unit comprising a health file utilizer access unit (not shown).

The health file user access unit in the health file access control system in the electronic medical cloud according to the second example is referred to here as user B access unit, the working principle is outlined as follows: user B access unit includes a health file owner access unit, therefore, the user B can not only input the basic information and/or health care information of the user B through the health file owner access unit to generate a health file, but also encrypt the generated health file through the health file utilizer access unit to generate a privacy-protected health file ciphertext, then send the privacy-protected health file ciphertext to the electronic medical cloud storage unit for storage.

In this system, the user B can only encrypt the user B's own health file, but cannot decrypt user B's privacy-protected health file or other users' privacy-protected health files in order to obtain the corresponding health files for review.

Figure 7:
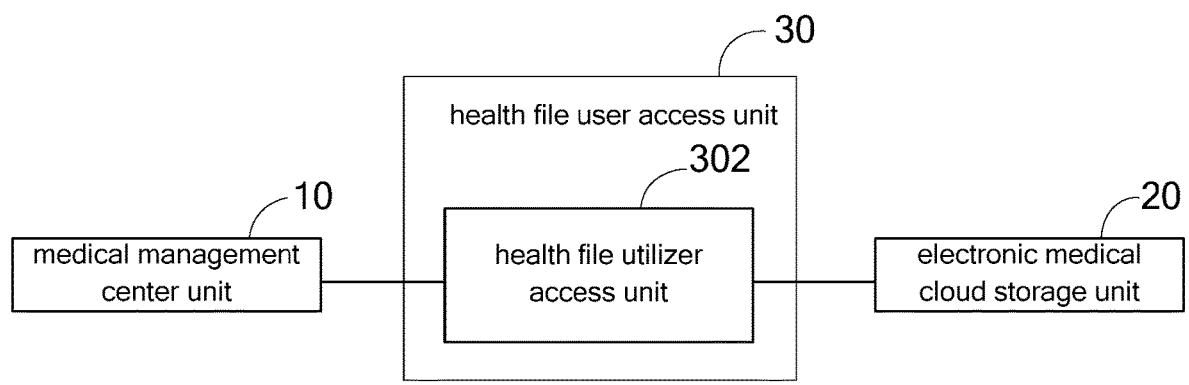
FIG. 7 depicts a block diagram showing a module structure of a third example of a health file access control system in an electronic medical cloud according to the present invention.

FIG. 7 depicts a block diagram showing a module structure of a third example of a health file access control system in an electronic medical cloud according to the present invention. As shown in FIG. 7, the health file access control system in the electronic medical cloud comprises: a medical management center unit 10, an electronic medical cloud storage unit 20, and a health file user access unit 30; wherein the medical management center unit 10 is configured to generate a system public key and a system private key, and generate a private key for corresponding utilizer's attributes according to the system public key, the system private key, and a set of utilizer's attributes sent by the health file user access unit 30; the electronic medical cloud storage unit 20 is configured to receive and store a privacy-protected health file ciphertext sent by the health file user access unit comprising a health file owner access unit (not shown); and the health file user access unit 30 is connected to the medical management center unit 10 and the electronic medical cloud storage unit 20, respectively and configured to generate the set of utilizer's attributes and decrypt the privacy-protected health file ciphertext sent by the electronic medical cloud storage unit 20 according to the system public key and the private key for utilizer's attributes sent by the medical management center unit 10.

Further, as shown in FIG. 7, the health file user access unit 30 includes a health file utilizer access unit 302 connected to the medical management center unit 10 and the electronic medical cloud storage unit 20, respectively and configured to generate a set of utilizer's attributes and decrypt the privacy-protected health file ciphertext sent by the electronic medical cloud storage unit 20 according to the system public key and the private key for utilizer's attributes sent by the medical management center unit 10.

The medical management center unit 10 is specifically configured to: (1) perform system initialization to generate a system public key and a system private key, and disclose the system public key and keep the system private key confidential; and (2) execute health file user registration and generate a private key for corresponding utilizer's attribute according to the system public key, the system private key, and a set of utilizer's attribute sent by the health file utilizer access unit 302.

The electronic medical cloud storage unit 20 is further configured to: (1) receive and store a privacy-protected health file ciphertext sent by the health file user access unit comprising a health file owner access unit (not shown); and (2) send the stored privacy-protected health file ciphertext to the health file utilizer access unit 302.

The health file utilizer access unit 302 is further configured to: (1) download the privacy-protected health file ciphertext from the electronic medical cloud storage unit 20; (2) input basic information of the health file utilizer; (3) generate a set of utilizer's attribute according to the input basic information of the health file utilizer; (4) parse the privacy-protected health file ciphertext sent by the electronic medical cloud storage unit 20 into a file symmetric ciphertext and a symmetric key ciphertext; (5) perform attribute-hiding attribute-based decryption on the symmetric key ciphertext according to the private key for utilizer's attribute sent by the medical management center unit 10 to obtain a symmetric key; and (6) perform a decryption algorithm of the advanced encryption standard for the file symmetric ciphertext according to the system public key sent by the medical management center unit 10 and the symmetric key obtained by performing attribute-hiding attribute-based decryption on the symmetric key ciphertext to obtain a health file.

In particular, the health file utilizer access unit 302 may download the privacy-protected health file from the electronic medical cloud storage unit 20 in various ways. For example, the health file utilizer access unit 302 may generate target information comprising pre-downloaded privacy-protected health file ciphertext and send the target information to the electronic medical cloud storage unit 20. The electronic medical cloud storage unit 20 sends the corresponding privacy-protected health file ciphertext to the health file utilizer access unit 302 according to the target information. Of course, those skilled in the art can also select other methods if necessary, which are not limited herein.

The health file access control system in the electronic medical cloud of the third example further comprises a communication network unit (not shown) connected to the medical management center unit 10, the electronic medical cloud storage unit 20, and the health file utilizer access unit 302, respectively in a wireless or wired manner for communication between the medical management center unit 10 and the health file utilizer access unit 302, and/or between the electronic medical cloud storage unit 20 and the health file utilizer access unit 302.

Figure 8:
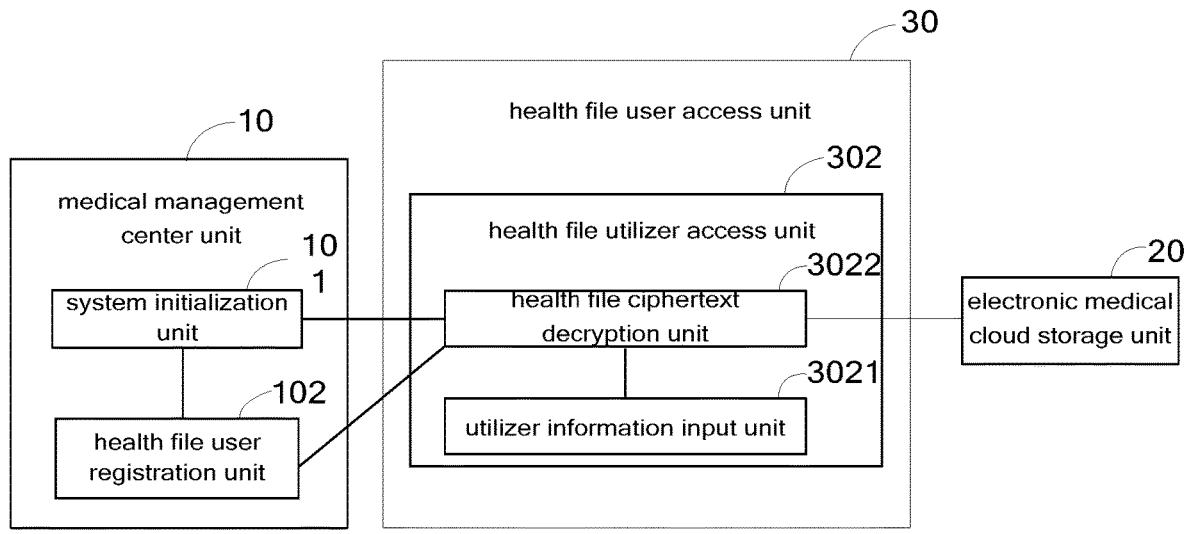
FIG. 8 depicts a block diagram showing another module structure of a third example of a health file access control system in an electronic medical cloud according to the present invention.

In some embodiments of the third example, as shown in FIG. 8, the medical management center unit 10 comprises a system initialization unit 101 and a health file user registration unit 102; the health file utilizer access unit 302 in the health file user access unit 30 comprises a utilizer information input unit 3021 and a health file decryption unit 3022; the system initialization unit 101 is configured to perform system initialization to generate a system public key and a system private key, and disclose the system public key and keep the system private key confidential; the health file user registration unit 102 is connected to the system initialization unit 101 and the health file ciphertext decryption unit 3022, respectively and configured to perform health file user registration and generate a private key for utilizer's attribute according to the system public key sent by the system initialization unit 101 and the set of utilizer's attributes sent by the health file ciphertext decryption unit 3022; the utilizer information input unit 3021 is configured to input basic information of the health file utilizer; the health file ciphertext decryption unit 3022 is connected to the system initialization unit 101, the electronic medical cloud storage unit 20, and the utilizer information input unit 3021, respectively and configured to generate a set of utilizer's attributes according to the basic information of the health file utilizer sent by the utilizer information input unit 3021, and decrypt on the privacy-protected health file ciphertext sent by the electronic medical cloud storage unit 20 according to the system public key sent by the system initialization unit 101 and the private key for utilizer's attributes sent by the health file user registration unit 102.

Further, the health file ciphertext decryption unit 3022 is further configured to: (1) download the privacy-protected health file ciphertext from the electronic medical cloud storage unit 20; (2) generate a set of utilizer's attribute according to basic information of the health file utilizer sent by the utilizer information input unit 3021; (3) parse the privacy-protected health file ciphertext sent by the electronic medical cloud storage unit 20 into a file symmetric ciphertext and a symmetric key ciphertext; (4) perform attribute-hiding attribute-based decryption on the symmetric key ciphertext according to the private key for utilizer's attribute sent by the health file user registration unit 102 to obtain a symmetric key; and (5) perform a decryption algorithm of the advanced encryption standard for the file symmetric ciphertext according to the system public key sent by the system initialization unit 10 and the symmetric key obtained by performing attribute-hiding attribute-based decryption on the symmetric key ciphertext to obtain a health file.

Specifically, the health file ciphertext decryption unit 3022 may download the privacy-protected health file from the electronic medical cloud storage unit 20 in various ways. For example, the health file ciphertext decryption unit 3022 may generate target information comprising pre-downloaded privacy-protected health file ciphertext and send the target information to the electronic medical cloud storage unit 20. The electronic medical cloud storage unit 20 sends the corresponding privacy-protected health file ciphertext to the health file utilizer access unit 302 according to the target information. Of course, those skilled in the art can also select other methods as appropriate, which are not limited herein.

In some alternative embodiments, the system may further comprise a communication network unit (not shown) connected to the system initialization unit 101, the health file user registration unit 102, the electronic medical cloud storage unit 20, and the health file encryption unit 3022, respectively in a wireless or wired manner for communication between the system initialization unit 101 and the health file encryption unit 3022, and/or between the health file user registration unit 102 and the health file encryption unit 3022, and/or between the electronic medical cloud storage unit 20 and the health file encryption unit 3022.

The health file user access unit in the health file access control system in the electronic medical cloud according to the third example is referred to here as user C access unit, the working principle is outlined as follows: the user C access unit includes a health file utilizer access unit, therefore, the user C can only input the basic information and/or health care information of the health file utilizer through the health file utilizer access unit, download the privacy-protected health file ciphertext of user C or another user (for example, user A and/or user B) from the electronic medical cloud storage unit, and decrypt the privacy-protected health file ciphertext through the health file utilizer access unit to obtain the health file corresponding to the user C or another user (such as user A and/or user B) for review.

In this system, the user C can only decrypt the privacy-protected health file ciphertext of user C or another user to obtain the corresponding health file for review, but cannot encrypt the health file of user C or another user to generate the privacy-protected health file ciphertext.

In the health file access control system in the electronic medical cloud of the first to third examples, the set of utilizer's attributes includes at least one attribute comprising an attribute name and at least one attribute value corresponding to the attribute name.

In the health file access control system in the electronic medical cloud of the first to third examples, the attribute-hiding attribute-based decryption includes a decryption test and an attribute-based decryption; wherein the decryption test is configured to output a symmetric private key if the set of utilizer's attributes in the utilizer attribute private key matches the access policy in the privacy-protected health file ciphertext, and output a prompt which indicates that no access permission is granted if the set of utilizer's attributes in the utilizer attribute private key does not match the access policy in the privacy-protected health file ciphertext; and wherein the attribute-based decryption is configured to output the symmetric private key if the decryption test is successful. In this process, the number of bilinear pairs required for each decryption test is set constant and, therefore, does not increase with the complexity of the access policy.

It should be understood that the health file access control system in the electronic medical cloud provided by the present invention may comprise a plurality of health file user access units, each of which may be selected from those described in the first to third examples, which is not limited herein.

It is assumed that the health file access control system in the electronic medical cloud provided by the present invention comprises three health file user access units as those shown in FIGS. 3, 5 and 7 and referred to as user A access unit, user B access unit and user C access unit, respectively. For the detailed description of these units, refer to the specific descriptions of the first to third examples, and details are not repeated herein. The working principle of each health file user access unit in the health file access control system in the electronic medical cloud including the above three health file user access units is described in detail below.

With regard to the working principle of user A access unit, it includes a health file owner access unit and a health file utilizer access unit. Therefore, the user A is able to not only input the basic information and/or health care information of the user A through the health file owner access unit to generate a health file, but also encrypt the generated health file through the health file owner access unit to generate a privacy-protected health file ciphertext, and send the privacy-protected health file ciphertext to the electronic medical cloud storage unit for storage. Also, the user A is able to download his or her privacy-protected health file ciphertext or another user's (for example, user B and/or user C) privacy-protected health file from the electronic medical cloud storage unit, input basic information of the health file utilizer through the health file utilizer access unit, and decrypt the privacy-protected health file ciphertext through the health file utilizer access unit to obtain the health file corresponding to the user A or another user (such as user B and/or user C) for review. With regard to the working principle of user B access unit, it includes a health file owner access unit. Therefore, user B is only able to input the basic information and/or health care information of the user B through the health file owner access unit to generate a health file, encrypt the generated health file through the health file owner access unit to generate a privacy-protected health file ciphertext, and send the privacy-protected health file ciphertext to the electronic medical cloud storage unit for storage. With regard to the working principle of user C access unit, it includes a health file utilizer access unit. Therefore, user C is able to input the basic information and/or health care information of the health file utilizer through the health file utilizer access unit, download user's privacy-protected health file ciphertext or another user's (for example, user A and/or user B) privacy-protected health file ciphertext from the electronic medical cloud storage unit, and decrypt the privacy-protected health file ciphertext through the health file utilizer access unit to obtain the health file corresponding to the user C or another user (such as user A and/or user B) for review.

In this system, the user A is able to not only encrypt the user A's own health file to generate a privacy-protected health file ciphertext, but also decrypt user A's privacy-protected health file ciphertext or other users' privacy-protected health file ciphertext, whereby the corresponding health file is obtained for review; the user B is only able to encrypt the user B's own health file, but is not able to decrypt user B's privacy-protected health file ciphertext or other users' privacy-protected health file ciphertexts in order to obtain the corresponding health files for review; and the user C is only able to decrypt user C's privacy-protected health file ciphertext or other users' privacy-protected health file ciphertext to obtain the corresponding health files for review, but is not able to encrypt user C's health file or other users' health files to generate the privacy-protected health file ciphertext.

In each of the above embodiments, the health file user access unit 30 may be further configured to download the privacy-protected health file ciphertext from the electronic medical cloud storage unit 20. In particular, the health file utilizer access unit 302 may be further configured to download the privacy-protected health file ciphertext from the electronic medical cloud storage unit 20. More specifically, the health file ciphertext decryption unit 3022 may be further configured to download the privacy-protected health file ciphertext from the electronic medical cloud storage unit 20.

The health file access control system in an electronic medical cloud provided by the present invention establishes a secure electronic medical cloud information storage system, which realizes fine-grained access control of health files while protecting data confidentiality. The attribute privacy protection is achieved under the premise of ensuring the confidentiality of health files. That is, the health file owner is able to hide the attribute value corresponding to the access policy in the privacy-protected health file ciphertext, while the health file utilizer is allowed to perform an efficient decryption test without access policy attribute value, and determine whether the utilizer attribute private key is able to decrypt the health file ciphertext including the basic information and/or health care information of the health file owner. The size of the system public key is constant, computational complexity of the decryption test is low, only a constant bilinear pair is needed, and the decryption does not require attribute value information, thereby simplifying the system, and improving computational efficiency and protecting attribute privacy while preserving system security.

Figure 9:
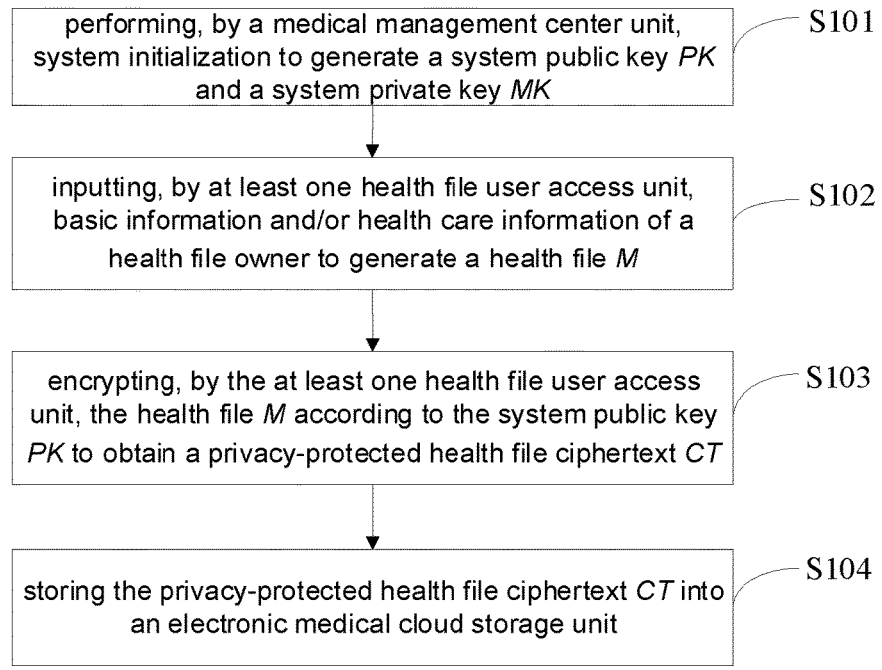
FIG. 9 depicts a flowchart illustrating a first example of a health file access control method in an electronic medical cloud according to the present invention.

FIG. 9 depicts a flowchart illustrating a first example of a health file access control method in an electronic medical cloud according to the present invention. As shown in FIG. 9, the method comprises the following steps:

performing, by a medical management center unit, system initialization to generate a system public key PK and a system private key MK (S101);

inputting, by at least one health file user access unit, basic information and/or health care information of a health file owner to generate a health file M (S102);

encrypting, by the at least one health file user access unit, the health file M according to the system public key PK to obtain a privacy-protected health file ciphertext CT (S103);

storing the privacy-protected health file ciphertext CT into an electronic medical cloud storage unit (S104).

The step of performing system initialization, by a medical management center unit, to generate a system public key PK and a system private key MK (S101) comprises:

selecting three parameters including G, $G_T$ and ê, wherein G is a cyclic group whose order is a composite number N; $G_T$ is another cyclic group whose order is a composite number N; ê is a bilinear pair; $N = p_1 p_2 p_3 p_4$, representing the product of four prime numbers $p_1$, $p_2$, $p_3$ and $p_4$; $G = G_{p1} \times G_{p2} \times G_{p3} \times G_{p4}$, representing the Cartesian product of four subgroups $G_{p1}$, $G_{p2}$, $G_{p3}$ and $G_{p4}$; ê: ê: $G \times G \to G_T$ is a mapping that satisfies bilinearity, non-degeneracy, and computability and that maps two elements in the cyclic group G to another element of another cyclic group $G_T$;

setting the attribute domain $U = Z\_N$ according to the selected three parameters G, $G_T$ and ê (S1012), wherein $Z_N$ is a finite set, $Z_N = \{1, 2, \ldots, N\}$;

selecting a random number $\alpha$, $a \in_R Z_N$, g, $h \in_R G_{p1}$, $X_3 \in_R G_{p3}$, Z, $X_4 \in_R G_{p4}$ (S1013);

It should be understood that the symbol $\in_R$ indicates random selection. Taking step S1013 as an example, $\alpha$, $a \in_R Z_N$ indicates that elements $\alpha$ and a are randomly selected from the set $Z_N$; g, $h \in_R G_{p1}$ indicates that g and h are randomly selected from the set $G_{p1}$; $X_3 \in_R G_{p3}$ indicates that $X_3$ is randomly selected from the set $G_{p3}$; and Z, $X_4 \in_R G_{p4}$ indicates that Z and $X_4$ are randomly selected from the set $G_{p4}$.

calculating $g^a$, $Y = ê(g, g)^\alpha$ and $H = hZ$ (S1014);

disclosing the system public key $PK = (N, g, g^a, Y, H, X_4)$ and keeping the system private key $MK = (\alpha, h, X_3)$ confidential (S1015);

The step of encrypting, by the at least one health file user access unit, the health file M according to the system public key PK to obtain a privacy-protected health file ciphertext CT (S103) comprises:

selecting a symmetric key $K_{se}$ from the key space of the advanced encryption standard according to the system public key PK, and performing a symmetric encryption algorithm of the advanced encryption standard for the health file M according to the symmetric key $K_{se}$ to obtain a file symmetric ciphertext $CT_{se}$ (S1031);

establishing an access policy $\mathbb{A}$ according to the system public key PK (S1032), wherein $\mathbb{A}=(A, \rho, \mathcal{T})$; A represents a matrix with l rows and n columns on $Z_N$; $\rho$ represents a mapping of a certain row of $\mathbb{A}$ to an attribute name; $\mathcal{T}$ represents a attribute value based on a row of A and $\rho$, $\mathcal{T}=(t_{\rho(1)}, t_{\rho(2)}, \ldots, t_{\rho(l)}) \in Z_N^l$; $Z_N^l$ represents a set of vectors with length l, each element in the vector is taken from $Z_N$;

selecting a random vector v, v'$\in_R Z_N^n$ (S1033), wherein v, v'$\in_R Z_N^n$ indicates that the vectors v and v' are randomly selected from the set $Z_N^n$, v=(s, $v_2, \ldots, v_n$), v'=(s', $v'_2, \ldots, v'_n$); $Z_N^n$ represents a set of vectors with length n, each element in the vector is taken from $Z_N$;

selecting a random number $Z_A \in_R G_{p4}$ based on $X_4$ and, for $1 \le x \le l$, selecting a random number $r_x \in_R Z_N$ and $Z_{A,x}$, $Z_{c,x}$, $Z_{d,x} \in_R G_{p4}$ (S1034), wherein $Z_A \in_R G_{p4}$ indicates that $Z_A$ is randomly selected from the set $G_{p4}$; $r_x \in_R Z_N$ indicates that $r_x$ is randomly selected from the set $Z_N$; $Z_{A,x}, Z_{c,x}, Z_{d,x} \in_R G_{p4}$ indicates that $Z_{A,x}, Z_{c,x}$ and $Z_{d,x}$ are randomly selected from the set $G_{p4}$;

calculating $\tilde{C}_A = Y^{s'}$, $\hat{C}_A = g^{s'} Z_A$, $\tilde{C}_1 = K_{se} \cdot Y^s$ and $\hat{C}_1 = g^s$ (S1035);

for $1 \le x \le l$, calculating $C_{A,x} = g^{aA_x \cdot v'} (g^{t_{\rho(x)}} H)^{-s'} Z_{A,x}$, $C_{1,x} = g^{aA_x \cdot v} (g^{t_{\rho(x)}} H)^{-r_x} Z_{c,x}$ and $D_{1,x} = g^{r_x} Z_{d,x}$ (S1036);

making $CT_\mathbb{A} = ((A, \rho), \tilde{C}_A, \hat{C}_A, \{C_{A,x}\}_{1 \le x \le l}, \tilde{C}_1, \hat{C}_1, \{C_{1,x}, D_{1,x}\}_{1 \le x \le l})$ (S1037);

obtaining a privacy-protected health file ciphertext CT= $(CT_{se}, CT_\mathbb{A})$ (S1038).

Figure 10:
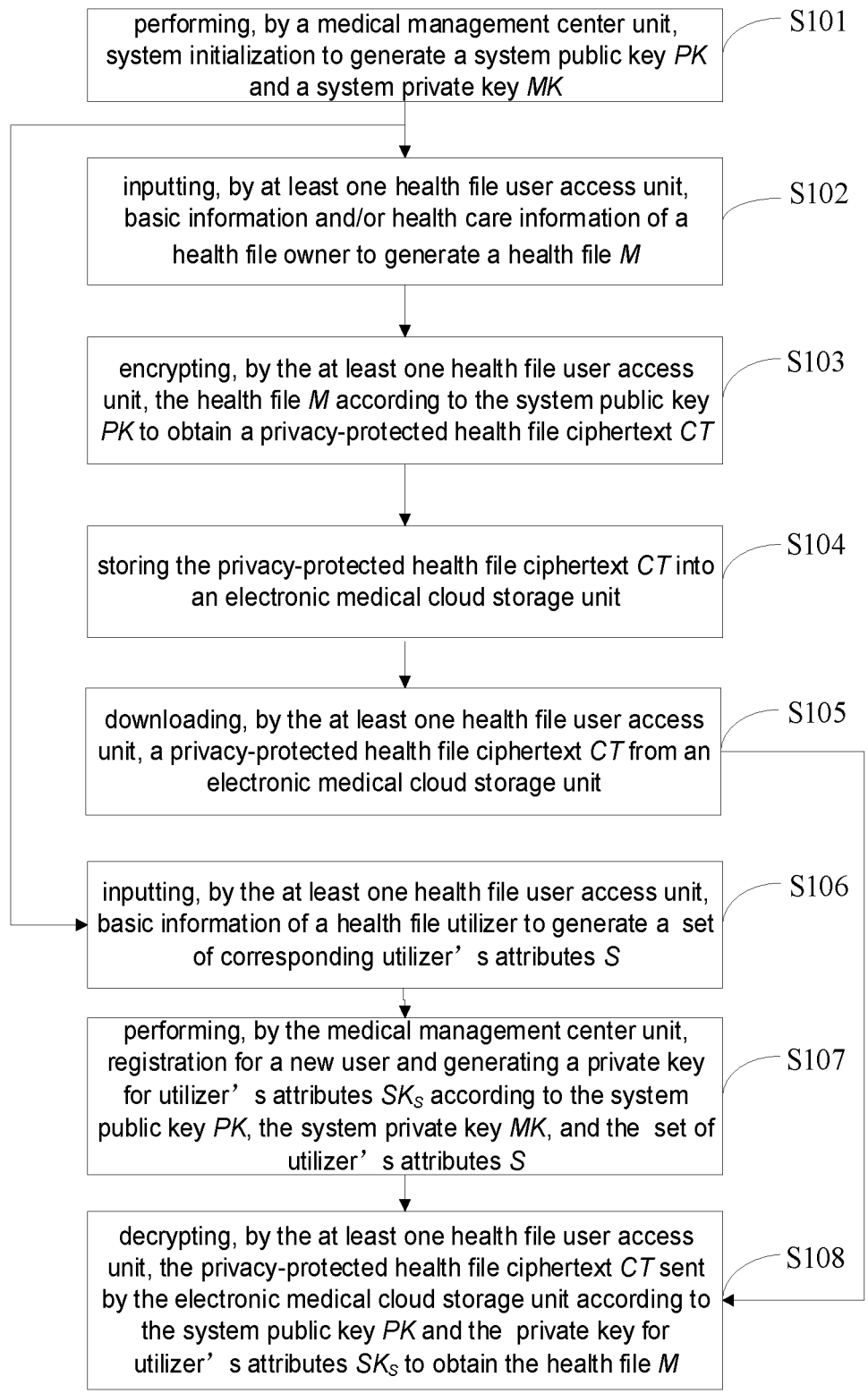
FIG. 10 depicts a flowchart illustrating a second example of a health file access control method in an electronic medical cloud according to the present invention.

FIG. 10 depicts a flowchart illustrating a second example of a health file access control method in an electronic medical cloud according to the present invention. As shown in FIG. 10, the method comprises the following steps:

performing, by a medical management center unit, system initialization to generate a system public key PK and a system private key MK (S101);

inputting, by at least one health file user access unit, basic information and/or health care information of a health file owner to generate a health file M (S102);

encrypting, by the at least one health file user access unit, the health file M according to the system public key PK to obtain a privacy-protected health file ciphertext CT (S103);

storing the privacy-protected health file ciphertext CT into an electronic medical cloud storage unit (S104);

downloading, by the at least one health file user access unit, a privacy-protected health file ciphertext CT from an electronic medical cloud storage unit (S105);

inputting, by the at least one health file user access unit, basic information of a health file utilizer to generate a set of corresponding utilizer's attributes S (S106);

performing, by the medical management center unit, registration for a new user and generating a private key for utilizer's attributes $SK_S$ according to the system public key PK, the system private key MK, and the set of utilizer's attributes (S107);

decrypting, by the at least one health file user access unit, the privacy-protected health file ciphertext CT sent by the electronic medical cloud storage unit according to the system public key PK and the private key $SK_S$ to obtain a health file M (S108).

The steps included in S101 and S103 in the second example are similar to those included in S101 and S103 in the first example, and are not repeated herein.

The step of performing, by the medical management center unit, registration for a new user and generating a private key for utilizer's attributes $SK_S$ according to the system public key PK, the system private key MK, and the set S (S107) comprises:

for each $i \in I_S$, based on $X_3$, selecting a random number $R_i \in_R G_{p3}$ (S1071); wherein, $S=(I_S, S)$ according to the system public key PK, the system private key MK, and the set S, wherein $S=(I_S, S)$ represents an set of index of the attribute name, $I_S \subseteq Z_N$; S represents a set of values of the attributes, $S = \{s_i \in Z_N\}_{i \in I_S}$; $R_i \in_R G_{p3}$ represents the element $R_i$ is randomly selected from the set $G_{p3}$;

selecting a random number $t \in_R Z_N$ and, based on $X_3$, selecting a random number R, R'$\in_R G_{p3}$ (S1072), wherein $t \in_R Z_N$ indicates that the element t is randomly selected from the set $Z_N$; R, R'$\in_R G_{p3}$ indicates that the element R and R' are randomly selected from the set $G_{p3}$;

calculating $K = g^\alpha g^{at} R$, $K' = g^\alpha R'$, for each $i \in I_S$, calculating $K_i = (g^{s_i} h)^t R_i$ (S1073);

obtaining the private key for utilizer's attributes $SK_S = (S, K, K', \{K_i\}_{i \in I_S})$ (S1074).

The step of decrypting, by the at least one health file user access unit, the privacy-protected health file ciphertext CT sent by the electronic medical cloud storage unit according to the system public key PK and the private key $SK_S$ to obtain a health file M (S108) comprises:

upon receiving the privacy-protected health file ciphertext CT, parsing the privacy-protected health file ciphertext CT into $CT = (CT_{se}, CT_\mathbb{A})$ (S1081);

performing attribute-hiding attribute-based decryption on the symmetric key ciphertext $CT_\mathbb{A}$ according to the system public key PK, the private key $SK_S$ based on the rules of the bilinear pair, to obtain a symmetric key $K_{se}$ (S1082); and performing a symmetric decryption algorithm of the advanced encryption standard for the file symmetric ciphertext $CT_{se}$ according to the system public key PK and the symmetric private key $K_{se}$ to obtain the health file M (S1083).

Further, the attribute-hiding attribute-based decryption includes a decryption test and an attribute-based decryption; wherein the decryption test is configured to output a symmetric private key $K_{se}$ if the set S in the utilizer attribute private key $SK_S$ matches the access policy $\mathbb{A}$ in the privacy-protected health file ciphertext CT, and output a prompt which indicates that no access permission is granted if the set S in the utilizer attribute private key $SK_S$ does not match the access policy $\mathbb{A}$ in the privacy-protected health file ciphertext CT; and wherein the attribute-based decryption is configured to output the symmetric private key if the decryption test is successful. In this process, the number of bilinear pairs required for each decryption test is constant and, therefore, the complexity of the access policy is not increased accordingly.

In particular, performing the attribute-hiding attribute-based decryption comprises:

determining that I matches (A, $\rho$) if a constant $\{w_i\}_{i \in I}$ on $Z_N$ satisfies $\Sigma_{i \in I} w_i A_i = (1, 0, \ldots, 0)$, and that I does not match (A, $\rho$) if the constant $\{w_i\}_{i \in I}$ on $Z_N$ does not satisfy $\Sigma_{i \in I} w_i A_i = (1, 0, \ldots, 0)$, wherein $A_i$ represents the ith row of matrix A, and I represents any subset of the set $\{1, 2, \ldots, l\}$;

determining that I is the smallest matching subset that matches (A, $\rho$) if $\mathcal{I}$ matches (A, $\rho$) and none of true subset of I matches (A, $\rho$);

calculating all the smallest matching subsets of the set I and (A, $\rho$), and marking the set of all the smallest matching subsets as $I_{A,\rho}$;

checking whether $I \in I_{A,\rho}$ exists, and both $\{\rho(i)|i \in I\} \subseteq I_S$ and $\tilde{C}_A^{-1} = \hat{e}(\prod_{i \in I} C_{A,i}^{w_i}, K')\hat{e}(\hat{C}_A, K^{-1} \prod_{i \in I} K_{\rho(i)}^{w_i})$ are satisfied; if I exists, calculating $$E = \frac{\hat{e}(\hat{C}_1, K)}{\prod_{i \in I}(\hat{e}(C_{1,i}K')\hat{e}(D_{1,i}, K_{\rho(i)}))^{w_i}}$$

and outputting a symmetric private key $K_{se} = \tilde{C}_1/E$ based on I and the corresponding $\{w_i\}_{i \in I}$; if I does not exist, outputting a prompt which indicates that no access permission is granted, wherein $\{w_i\}_{i \in I}$ is a constant on $Z_N$ that is determined by the match of I and $(A, \rho)$.

Figure 11:
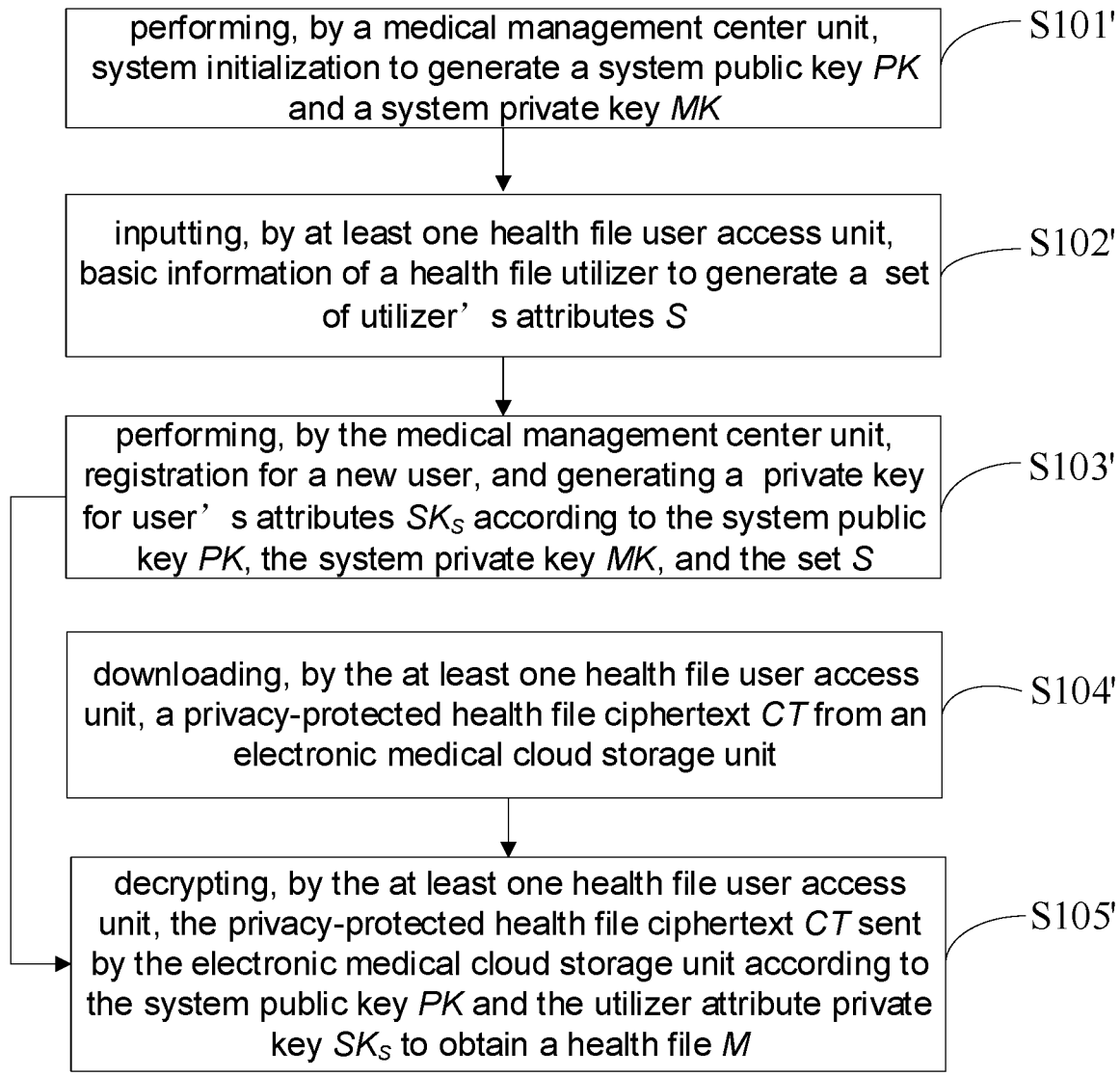
FIG. 11 depicts a flowchart illustrating a third example of a health file access control method in an electronic medical cloud according to the present invention.

FIG. 11 depicts a flowchart illustrating a third example of a health file access control method in an electronic medical cloud according to the present invention. As shown in FIG. 11, the method comprises the following steps:

performing, by a medical management center unit, system initialization to generate a system public key PK and a system private key MK (S101');

inputting, by at least one health file user access unit, basic information of a health file user to generate a set of utilizer's attributes S (S102');

performing, by the medical management center unit, registration for a new user, and generating a private key for user's attributes $SK_S$ according to the system public key PK, the system private key MK, and the set S (S103');

downloading, by the at least one health file user access unit, a privacy-protected health file ciphertext CT from an electronic medical cloud storage unit (S104'); and decrypting, by the at least one health file user access unit, the privacy-protected health file ciphertext CT sent by the electronic medical cloud storage unit according to the system public key PK and the private key $SK_S$ to obtain a health file M (S105').

The steps included in S101' in the third example are similar to those included in S101 in the first example, and the steps included in S103' and S105' in the third example are similar to those included in S107 and S108 in the second example, and are not repeated herein.

In the health file access control method in the electronic medical cloud of the first to third examples, the set of utilizer's attributes includes at least one attribute comprising an attribute name and at least one attribute value corresponding to the attribute name.

The health file access control method in an electronic medical cloud provided by the present invention establishes a secure electronic medical cloud information storage method, which realizes fine-grained access control of health files while keeping data confidential. The attribute privacy protection is achieved under the premise of ensuring the confidentiality of health files. That is, the health file owner is able to hide the attribute value corresponding to the access policy in the privacy-protected health file ciphertext, while the health file utilizer is able to perform an efficient decryption test without access policy attribute value, and determine whether the private key for utilizer's attributes is able to decrypt the health file ciphertext including the basic information and/or health care information of the health file owner. As the size of the system public key is constant, computational complexity of the decryption test is low, only a constant bilinear pair is needed, and the decryption does not require attribute value information, thereby simplifying the method, and improving computational efficiency and protecting attribute privacy while preserving method security.

It should be noted that the health file access control method in the electronic medical cloud provided by the present invention corresponds to the health file access control system in the electronic medical cloud provided by the present invention. In other words, the health file access control method in the electronic medical cloud provided by the present invention is implemented in the health file access control system in the electronic medical cloud provided by the present invention. The description of the method is also applicable to the system.

The present invention has been described in detail with reference to the embodiments thereof, however, it should be understood that the specific description herein are shall not be construed as limiting the scope of the invention, and various modifications made to the above embodiments after reading this specification by those skilled in the art fall within the scope of the present invention.

The invention claimed is:

1. A health file access control system in an electronic medical cloud, comprising:

a medical management center device comprising a processor and a storage, the processor configured to executed computerized codes from the storage to perform a method, the method generating a system public key and a system private key, and generate a private key for corresponding utilizer's attributes according to the system public key, the system private key, and a set of utilizer's attributes sent by the at least one health file user access device;

an electronic medical cloud storage unit configured to receive and store a privacy-protected health file ciphertext sent by the at least one health file user access device; and at least one health file user access device configured to encrypt the health file according to the system public key sent by the medical management center device to obtain the privacy-protected health file ciphertext, and/or generate the set of utilizer's attributes, and decrypt the privacy-protected health file ciphertext sent by the electronic medical cloud storage according to the system public key and the private key for utilizer's attributes sent by the medical management center device;

the method further selecting three parameters including G, $G_T$ and ê setting an attribute domain $U=Z_N$ to generate the system public key PK, PK=(N·g,$g^a$,Y,H, $X_4$) and a system private key MK; MK=($\alpha$,b,$X_3$); wherein G is a cyclic group whose order is a composite number N; $G_T$ is another cyclic group whose order is a composite number N; ê is a bilinear pair; N=$p_1p_2p_3p_4$ represents the product of four prime numbers $p_1$, $p_2$, $p_3$ and $p_4$; G=G×$G_{p2}$×$G_{p3}$×$G_{p4}$ represents the Cartesian product of four subgroups $G_{p1}$, $G_{p2}$, $G_{p3}$ and $G_{p4}$; ê:G×G→$G_T$ is a mapping that satisfies bilinearity, non-degeneracy, and computability and that maps two elements in the cyclic group G to another element of another cyclic group $G_T$; $Z_N$ is a finite set, $Z_N$= {1, 2, . . . , N}l; a is a random number; $\alpha$,a$\in_R Z_N$, g, h$\in_R G_{p1}$, $X_3 \in_R G_{p3}$, and Z, $X_4 \in_R G_{p4}$; Y=ê(g,g)$^\alpha$ and H=hZ.

2. The health file access control system in an electronic medical cloud according to claim 1, further comprising a communication network configured to provide wireless or wired communication between the medical management center device and the at least one health file user access device, and/or between the electronic medical cloud storage and the at least one health file user access device.

3. The health file access control system in an electronic medical cloud according to claim 1, wherein the health file user access device includes a health file owner access device configured to encrypt the health file according to the system public key to obtain the privacy-protected health file ciphertext and a health file utilizer access device configured to generate the set of utilizer' attributes and decrypt the privacy-protected health file ciphertext sent by the electronic medical cloud storage according to the system public key and the private key for utilizer's attributes sent by the medical management center device; or the health file user access device includes a health file owner access device configured to encrypt the health file according to the system public key to obtain the privacy-protected health file ciphertext; or the health file user access device includes a health file utilizer access device configured to generate the set of utilizer's attributes and decrypt the privacy-protected health file ciphertext sent by the electronic medical cloud storage according to the system public key and the private key for utilizer's attributes sent by the medical management center device.

4. The health file access control system in an electronic medical cloud according to claim 1, wherein the medical management center device comprises:

a system initialization device configured to perform system initialization to generate the system public key and the system private key, and disclose the system public key and keep the system private key confidential; and a health file user registration device configured to execute health file user registration and generate the private key for utilizer's attributes according to the system public key, the system private key, and the set for utilizer's attributes sent by the system initialization device.

5. The health file access control system in an electronic medical cloud according to claim 3, wherein the health file owner access device comprises:

an owner information input device configured to input basic information and/or health care information of the health file owner to generate the health file; and a health file encryption device configured to encrypt the health file sent by the owner information input device according to the system public key to obtain the privacy-protected health file ciphertext, and send the privacy-protected health file ciphertext to the electronic medical cloud storage.

6. The health file access control system in an electronic medical cloud according to claim 5, wherein the health file encryption device is further configured to:

select a symmetric private key from the key space of the advanced encryption standard according to the system public key, and perform a symmetric encryption algorithm of the advanced encryption standard for the health file sent by the owner information input device according to the system public key and the symmetric private key to obtain a file symmetric ciphertext;

select an access policy according to the system public key sent;

perform attribute-hiding attribute-based encryption on the symmetric private key according to the access policy to generate a symmetric private key ciphertext; and generate the privacy-protected health file ciphertext according to the file symmetric ciphertext and the symmetric private key ciphertext, and send the privacy-protected health file ciphertext to the electronic medical cloud storage.

7. The health file access control system in an electronic medical cloud according to claim 3, wherein the health file utilizer access device comprises:

a utilizer information input device configured to input basic information of the health file utilizer; and a health file ciphertext decryption interface configured to generate the set of utilizer's attributes according to the basic information of the health file utilizer sent by the utilizer information input device, and decrypt the privacy-protected health file ciphertext sent by the electronic medical cloud storage according to the system public key and the private key for utilizer's attributes.

8. The health file access control system in an electronic medical cloud according to claim 7, wherein the health file decryption device is specifically configured to:

parse the privacy-protected health file ciphertext sent by the electronic medical cloud storage into the file symmetric ciphertext and the symmetric private key ciphertext;

perform attribute-hiding attribute-based decryption on the symmetric private key ciphertext according to the utilizer attribute private key to obtain the symmetric private key; and subject the file symmetric ciphertext to a decryption algorithm of the advanced encryption standard according to the system public key and the symmetric private key to obtain the health file.

9. The health file access control system in an electronic medical cloud according to claim 8, wherein the attribute-hiding attribute-based decryption comprises:

a decryption test configured to output the symmetric private key if the set of utilizer's attributes in the private key for utilizer's attributes matches the access policy in the privacy-protected health file ciphertext, and output a prompt which indicates that no access permission is granted if the set of utilizer's attributes in the private key for utilizer's attributes does not match the access policy in the privacy-protected health file ciphertext; and an attribute-based decryption configured to output the symmetric private key if the decryption test is successful.

10. The health file access control system in an electronic medical cloud according to claim 1, wherein the set of utilizer's attributes includes at least one attribute comprising an attribute name and at least one attribute value corresponding to the attribute name.

11. A health file access control method in an electronic medical cloud, comprising:

performing, by a medical management center device, system initialization to generate a system public key PK and a system private key MK (S101);

inputting, by at least one health file user access device, basic information and/or health care information of a health file owner to generate a health file M (S102);

encrypting, by the at least one health file user access device the health file M according to the system public key PK to obtain a privacy-protected health file ciphertext CT (S103); and storing the privacy-protected health file ciphertext CT into an electronic medical cloud storage unit (S104);

wherein the S101 specifically comprises:

selecting three parameters including G, $G_T$ and ê, wherein G is a cyclic group whose order is a composite number N; $G_T$ is another cyclic group whose order is a composite number N; ê is a bilinear pair; $N=p_1p_2p_3p_4$ represents the product of four prime numbers $p_1$, $p_2$, $p_3$ and $p_4$; $G=G\times G_{p2}\times G_{p3}\times G_{94}$ represents the Cartesian product of four subgroups $G_{p1}$, $G_{p2}$, $G_{p3}$ and $G_{p4}$; ê:$G\times G\rightarrow G_T$ is a mapping that satisfies bilinearity, non-degeneracy, and computability and that maps two elements in the cyclic group G to another element of another cyclic group $G_T$;

setting an attribute domain $U=Z_N$ according to the selected three parameters G, $G_T$ and ê (S1012), wherein $Z_N$ is a finite set, $Z_N=\{1, 2, \ldots, N\}$;

selecting a random number, $\alpha, a \in_R Z_N$, $g,h\in_R G_{p1}$, $X_3\in_R G_{p3}$, and $Z,X_4\in_R G_{p4}$ (S1013);

calculating $g^\alpha$, $Y=\hat{e}(g,g)^\alpha$ and $H=hZ$ (S1014); and disclosing the system public key $PK=(N,g,g^\alpha,Y,H,X_4)$ and keeping the system private key $MK=(\alpha,h,X_3)$ confidential (S1015).

12. The health file access control method in an electronic medical cloud according to claim 11, further comprising:

downloading, by the at least one health file user access device; a privacy-protected health file ciphertext CT from an electronic medical cloud storage (S105);

inputting, by the at least one health file user access device; basic information of a health file utilizer to generate a set of corresponding utilizer's attributes S (S106);

performing, by the medical management center device, registration for a new user and generating a private key for utilizer's attributes SKS according to the system public key PK, the system private key MK, and the set of utilizer's attributes PK (S107);

decrypting, by the at least one health file user access device; the privacy-protected health file ciphertext CT sent by the electronic medical cloud storage according to the system public key PK and the private key for utilizer's attributes SKS to obtain the health file M (S108).

13. The health file access control method in an electronic medical cloud according to claim 11, wherein the S103 specifically comprises:

selecting a symmetric private key $K_{se}$ from the key space of the advanced encryption standard according to the system public key PK, and performing a symmetric encryption algorithm of the advanced encryption standard for the health file M according to the symmetric private key $K_{se}$ to obtain a file symmetric ciphertext $CT_{se}$ (S1031);

establishing an access policy 𝔸 according to the system public key PK (S1032), wherein $\mathbb{A}=(A,\rho,\mathcal{T})$; A represents a matrix of l rows and n columns on $Z_N$; $\rho$ represents a mapping of a certain row of 𝔸 to an attribute name; $\mathcal{T}$ represents a attribute value corresponding to the row of A based on $\rho$, $\mathcal{T}=(t_{p(1)}, t_{p(2)},\ldots, t_{p(l)})\in Z_N^l$; $Z_N^l$ represents a set of vectors with length l, each element in the vector is taken from $Z_N$;

selecting a random vector $v,v'\in_R Z_N^n$ (S1033), wherein $v,v'\in_R Z_N^n$ indicates that the vectors v and v' are randomly selected from the set $Z_N^n$, $v=(s, v_2, \ldots, v_n)$, $v'=(s', v'_2, \ldots, v'_n)$; $Z_N^n$ represents a set of vectors with length n, each element in the vector is taken from $Z_N$;

selecting a random number $Z_\Delta\in_R G_{p4}$ based on $X_4$ and, for $1\leq x\leq l$, selecting a random number $r_x\in_R Z_N$ and $Z_{\Delta,x}$, $Z_{c,x}, Z_{d,x}\in_R G_{p4}$ (S1034), calculating $\tilde{C}_\Delta=Y^{s'}$, $\hat{C}_\Delta=g^{s'}Z_\Delta$, $\tilde{C}_1=K_{se}\cdot Y^s$ and $\hat{C}_1=g^s$ (S1035);

for $1\leq x\leq l$, calculating $C_{\Delta,x}=g^{aA_xv'}(g^{t_{p(x)}}H)^{-s'}Z_{\Delta,x}$, $C_{1,x}=g^{aA_xv}(g^{t_{p(x)}}H)^{-r_x}Z_{c,x}$ and $D_{1,x}=g^{r_x}Z_{d,x}$ (S1036);

making a symmetric private key ciphertext $C T_\mathbb{A}=((A,\rho),\tilde{C}_\Delta, \hat{C}_\Delta, \{C_{\Delta,x}\}_{1\leq x\leq l}, \tilde{C}_1, \hat{C}_1, \{C_{1,x}, D_{1,x}\}_{1\leq x\leq l})$ (S1037); and obtaining a privacy-protected health file ciphertext $CT=(CT_{se}, CT \mathbb{A})$ (S1038).

14. The health file access control method in an electronic medical cloud according to claim 11, wherein the S107 specifically comprises:

for each $i\in IS$, based on $X_3$, selecting a random number $R_i\in_R G_{p3}$ according to the system public key PK, the system private key MK, and the set of utilizer's attributes S (S1071), wherein $S=(I_S, S)$, $I_S$ represents an set of indexes of the attribute names, $I_S\subseteq Z_N$; S represents a set of attribute values, $S=\{s_i\in Z_N\}_{i\in I_s}$; $R_i\in_R G_{p3}$ represents the element $R_i$ is randomly selected from the set $G_{p3}$;

selecting a random number $t\in_R Z_N$ and, based on $X_3$, selecting a random number $R,R'\in_R G_{p3}$ (S1072);

calculating $K=g^\alpha g^{at}R$, $K'=g^\alpha R'$, and for each $i\in I_s$, calculating $K_i=(g^s h)^t R_i$ (S1073); and obtaining the private key for utilizer's attributes $SK_S=(S, K,K',\{K_i\}_{i\in I_s})$ (S1074).

15. The health file access control method in an electronic medical cloud according to claim 14, wherein the S108 specifically comprises:

upon receiving the privacy-protected health file ciphertext CT, parsing the privacy-protected health file ciphertext CT into $CT=(CT_{se}, CT \mathbb{A})$ (S1081);

performing attribute-hiding attribute-based decryption on the symmetric private key ciphertext CT 𝔸 according to the system public key PK, the private key for utilizer's attributes $SK_S$ based on the riles of the bilinear pair, to obtain a symmetric private key $K_{se}$ (S1082); and performing a symmetric decryption algorithm of the advanced encryption standard for the file symmetric ciphertext $CT_{se}$ according to the system public key PK and the symmetric private key $K_{se}$ to obtain the health file M (S1083).

16. The health file access control method in an electronic medical cloud according to claim 15, wherein performing the attribute-hiding attribute-based decryption specifically comprises:

outputting the symmetric private key $K_{se}$ if the set of utilizer's attributes S in the private key for utilizer's attributes $SK_S$ matches the access policy 𝔸 in the privacy-protected health file ciphertext CT, and outputting a prompt which indicates that no access permission is granted if the set of utilizer's attributes S in the private key for utilizer's attributes $SK_S$ does not match the access policy 𝔸 in the privacy-protected health file ciphertext CT.

17. The health file access control method in an electronic medical cloud according to claim 15, wherein performing the attribute-hiding attribute-based decryption specifically comprises:

determining that I matches $(A,\rho)$ if a constant $\{w_i\}_{i\in I}$ on $Z_N$ satisfies $\Sigma_{i\in I}w_iA_i=(1, 0, \ldots, 0)$, and that I does not match $(A,\rho)$ if the constant $\{w_i\}_{i\in I}$ on $Z_N$ does not satisfy $\Sigma_{i\in I}w_iA_i=(1, 0, \ldots, 0)$, wherein $A_i$ represents the ith row of matrix A, and I represents any subset of the set $\{1, 2, \ldots, l\}$;

determining that I is the smallest matching subset that matches $(A,p)$ if I matches $(A,\rho)$ and any true subset of I does not match $(A, \rho)$;

calculating all the smallest matching subsets of the set I and $(A,\rho)$ and marking the set of all the smallest matching subsets as $I_{A,\rho}$; and checking whether $I \in I_{A,\rho}$ exists, and both $\{\rho(i) \in i \in I\} \subseteq I_S$ and $\tilde{C}_\Delta^{-1} = \hat{e}(\Pi_{i \in I} C_{\Delta,i}^{w_i}, K')\hat{e}(\tilde{C}_\Delta, K^{-1}\emptyset_{i \in I} K_{\rho(i)}^{w_i})$ are satisfied; if exists, calculating $$E = \frac{\hat{e}(\hat{C}_1, K)}{\prod_{i \in I}(\hat{e}(C_{1,i}K')\hat{e}(D_{1,i}, K_{\rho(i)}))^{w_i}}$$

and outputting a symmetric private key $K_{se} = \tilde{C}_1/E$ based on I and the corresponding $\{w_i\}_{i \in I}$; if I does not exist, outputting a prompt which indicates that no access permission is granted, wherein $\{w_i\}_{i \in I}$ is a constant on $Z_N$ that is determined by the matching of I and $(A,\rho)$.

18. The health file access control method in an electronic medical cloud according to claim 11, wherein the set of utilizer's attributes includes at least one attribute comprising an attribute name and at least one attribute value corresponding to the attribute name.

19. A health file access control method in an electronic medical cloud, comprising:
   performing, by a medical management center device, system initialization to generate a system public key PK and a system private key MK (S101');
   inputting, by at least one health file user access device, basic information of a health file utilizer to generate a set of utilizer's attributes S (S102');
   performing, by the medical management center device, registration for a new user and generating a private key for utilizer's attributes SKS according to the system public key PK, the system private key MK, and the set of utilizer's attributes PK (S107);
   downloading, by the at least one health file user access device, a privacy-protected health file ciphertext CT from an electronic medical cloud storage (S104'); and
   decrypting, by the at least one health file user access device; the privacy-protected health file ciphertext CT sent by the electronic medical cloud storage according to the system public key PK and the private key for utilizer's attributes SKS to obtain a health file M (S105').

* * * * *